(12) United States Patent
Narayanan et al.

(10) Patent No.: US 6,187,715 B1
(45) Date of Patent: Feb. 13, 2001

(54) WATER-BASED MICROEMULSIONS OF A LOWER ALKYL ESTER OF QUINOXALINYL HERBICIDE

(75) Inventors: Kolazi S. Narayanan, Wayne, NJ (US); Domingo I. Jon, New York, NY (US); Donald I. Prettypaul, Englewood, NJ (US)

(73) Assignee: ISP Investments Inc., Wilmington, DE (US)

( * ) Notice: Under 35 U.S.C. 154(b), the term of this patent shall be extended for 0 days.

(21) Appl. No.: 09/505,306

(22) Filed: Feb. 16, 2000

(51) Int. Cl.⁷ .................................................. A01N 63/00
(52) U.S. Cl. ............................................... 504/118
(58) Field of Search .............................. 504/118

(56) References Cited

U.S. PATENT DOCUMENTS 4,931,089 * 6/1990 Martin ..................................... 71/121
5,576,269 * 11/1996 Hirabayashi et al. ............... 504/236

FOREIGN PATENT DOCUMENTS

9423578 * 10/1994 (WO) .

\* cited by examiner

*Primary Examiner*—S. Mark Clardy
*Assistant Examiner*—Alton Pryor
(74) *Attorney, Agent, or Firm*—Marilyn J. Maue; William J. Davis; Walter Katz

(57) ABSTRACT

Clear, high load water miscible emulsions of quinoxalinyl ester herbicides, particularly quizalofop-p-ethyl, as a single phase, translocatable composition which is free of xylene and alkylphenol ethoxylate surfactants and concentrate matrix for the active quinoxalinyl ester component at between about 9 and about 25 wt. % active concentration.

9 Claims, No Drawings

WATER-BASED MICROEMULSIONS OF A LOWER ALKYL ESTER OF QUINOXALINYL HERBICIDE

DESCRIPTION OF THE PRIOR ART

Agriculturally active chemicals are most preferably applied in the form of aqueous emulsions, solutions or suspensions. Occasionally, they may also be applied in the form of a dust wherein the active ingredient is adsorbed onto or mixed with a finely divided inert carrier material, such as, china clay, or the like. With such powdered or dust compositions, drift due to wind is a problem and consequently, liquid formulations are preferred.

One of the problems with such liquid formulations is the fact that chemicals possessing agricultural activity, particularly those high load active concentrations often exhibit extreme insolubility in water. This results in their having to be dissolved either in organic solvents or utilized in the form of emulsions subsequent to phase separation or suspensions. With respect to the use of organic solvents, such as xylene, or phenolic esters, these are generally disadvantageous from an environmental and cost viewpoint. Particularly, such organic chemicals may exhibit toxicity or side-effects which may be adverse to the effect of the agricultural chemical itself or to the subsequent fruit or vegetable produced in the particular agricultural use. This toxicity may also be disadvantageous with respect to inhalation during handling and flammability.

When attempts are made to provide emulsified or suspension formulations, difficulties are encountered with respect to providing a desirably high concentration of the agriculturally active ingredient. Thus, when such agriculturally active chemicals are formulated into a macroemulsion (sometimes referred to herein as an emulsion), it is difficult to maintain the emulsified state. This, in turn, creates problems in maintaining a uniform formulation and subsequent plant dosage, particularly, when the formulation is diluted with water for application on the plants.

U.S. Pat. No. 5,317,042 disclosed a clear stable, efficacious aqueous microemulsion of an agriculturally active chemical, alone, or in a complex mixture, obtained by incorporating the chemical in an inert matrix composition containing a defined mixture of nonionic surfactant to form a microemulsion concentrate which is subsequently diluted with water for plant treatment. Patentee's inert matrix composition consists of a predetermined mixture of nonionic surfactants which include nonylphenol ethoxylate having an HLB of >6. However, the presence of nonylphenol ethoxylate in the formulation is considered detrimental from an ecological standpoint.

Accordingly, it is an object of this invention to provide a substantially stable homogeneous, water soluble microemulsion containing at least 9 wt. % of a quinoxalinyl ester herbicide which is free of toxic and environmentally objectionable surfactants.

Another object is to provide a stable concentrate containing quizalofop-p-ethyl as the active herbicide in high load which is readily soluble in water and suitable for spraying crops.

These and other benefits and objectives will become apparent from the following description and disclosure.

SUMMARY OF THE INVENTION

In accordance with the present invention there is provided a stable, liquid homogeneous concentrate matrix comprising MICROFLEX admixed with a heavy aromatic petroleum oil distillate boiling between 100° F. and 250° F., combined in a weight ratio of between about 1–5:1 MICROFLEX to oil. Although an excess of oil, up to about 1:9 can be used for some purposes; such compositions are not desirable for treating crops since they require the addition of substantial amounts of one or more emulsifiers to obtain a homogeneous liquid composition after dilution of the concentrate with water. Such high concentrations of emulsified often causes crop burn and adds considerably to the cost of the composition.

The present concentrate can be diluted with up to 99.9 wt. % water to provide a homogeneous liquid spray for treating plants. The general formula for the MICROFLEX composition is described in the SUMMARY OF THE INVENTION, elements (b) through (f) in copending U.S. patent application Ser. No. 09/098,658, filed Jun. 17, 1998. The teaching of this application is incorporated herein by reference.

The above matrix concentrate is capable of loading up to 25 wt. % of an active phenoxy carboxylate ester such as a quinoxalinyl ester herbicide or insecticide, which includes such compounds as quizalofop-p-ethyl ester, quizalofop-p-tefuryl tetrahydrofurfuryl ester, a $C_1$ to $C_4$ ester of a halogenated quinoxalinyl oxyphenoxy compound, e.g. chloro quinoxalinyl oxyphenoxy propionate, 2,4-dichloro phenoxy ethyl butyrate, 1,4-dichloro phenoxy ethyl propionate, 2,4-dichloro phenoxy butyl propionate, etc.

DETAILED DESCRIPTION OF THE INVENTION

The basic concentrate of this invention comprises a mixture of MICROFLEX and a heavy aromatic petroleum oil distillate; however, since the distillate is strongly hydrophobic, to achieve a clear, homogeneous composition upon dilution, the ratio of oil should not exceed 1:1. More desirably a weight ratio of between about 2:1 and about 5:1 MICROFLEX to oil distillate is employed to obtain a homogeneous sprayable solution.

The oil distillates suitably employed for the present MICROFLEX mixture have an average boiling point of between 100° and 250° F. and are commercially available as fractions from crude oil distillation. Typical of such oils are Exxon 200, Aromatic 150, Aromatic 200 available from Exxon and Texaco 400. Generally these oil fractions contain a major portion of aromatic solvent naphtha and a minor portion of middle distillate solvent extract of which about a 55–65/35–45 mixture is most desirable. Normally these oils, which contain predominantly aromatics, are compounds having 8 to 15 carbon atoms and primarily 10–12 carbon atoms. The flash point of these distillates is preferably above 200° F.

As indicated above the MICROFLEX composition of this invention is a mixture and contains
  (i) 0 to about 60 wt. %, preferably 0.15 to 40 wt. %, of a N- $C_1$ to $C_4$ alkyl lactam such as an N-alkyl pyrrolidone, an N-alkyl caprolactam or mixtures thereof;
  (ii) from about 0.002 to about 40 wt. %, preferably 0.05 to 29 wt. % of a N- $C_8$ to $C_{18}$ alkyl lactam such as an N-alkyl pyrrolidone, an N-alkyl caprolactam and mixtures thereof,
  (iii) 0 to abut 30 wt. %, preferably 0.5 to 15 wt. %, of an ethylene oxide/propylene oxide block copolymer surfactant;
  (iv) 0.03 to about 80 wt. %, preferably 40 to 70 wt. %, of an alkoxylated castor oil, tristyryl phenol ethoxylate or a mixture thereof and
  (v) 0 to about 10 wt. %, preferably 0.005 to 6 wt. % of a phosphate ester buffer.

In the above MICROFLEX composition, N-methyl- and N-octyl- lactams, particularly N-methyl- and N-octylpyrrolidones, are preferred. Although the above lactams can be ring substituted with $C_1$ to $C_4$ alkyl radicals, unsubstituted species are more desirable.

In general, the present concentrate containing the active component is prepared by initially combining MICROFLEX as an anhydrous mixture with the oil fraction and then gradually adding between about 9 to about 25% by weight of the active component. This operation can be carried out under continuous agitation over a period of from about 0.5 to about 6 hours at ambient temperature up to a temperature below the boiling point of the oil. The resulting mixture is a substantially clear, somewhat viscous liquid which can be diluted with up to 99.9 wt. % of water to form a stable microemulsion suitable for treating a plant area. The concentrate when diluted with either soft or (100–600 ppm) hard water is stable at both low and high temperatures over the two-week period tested. The concentration of the active component in the diluted concentrate can vary widely depending on the dosages conventionally recommended, the type of plant to be treated, the atmospheric conditions encountered in field spraying etc. Usually an active concentration of between about 0.01 and about 5 wt. %, more often, between about 0.1 and about 1.5 wt. %, is sufficient to exert a herbicidal affect. Because of the present matrix, the admixed agrochemical possesses superior translocation capability both in the xylem and in the phloem of the plant and can be applied at any stage of plant development. The emulsion is also effective in preventing seed maturation and therefore possesses both pre-emergent and post emergent properties. The herbicidal spray compositions are particularly useful against graminaceous weed species. The present microemulsion is also compatible with mixtures of herbicidal and/or plant growth regulating or other agriculturally active chemicals employed for the treatment of plants. Unexpectedly, the present matrix not only promotes water solubility of water insoluble active compounds or their compositions, but also promotes the solubility of the hydrophobic oil in the composition so that a homogeneous liquid is obtained and is stable over a broad range of temperatures and at high loads of active component. This function of the matrix is particularly advantageous when incorporating highly insoluble active compounds which must be added to a matrix in an oil composition.

The concentrates of this invention, containing or omitting the active component, can be supplied to the consumer for on-site formulation which may or may not include the dilution with water and/or the addition of one or more active agents.

Inert excipients can be added to the concentrate or to the diluted concentrate when desired. Accordingly, such additives as a wetting agent, e.g. a dialkyl polysiloxane, a cosolvent, e.g. cyclohexanone, octanol, and other polar solvents and/or a spreading and sticking agent, e.g. phthalic glycerol, an alkyd resin and the like can be incorporated in these compositions. When employed, these excipients generally may comprise between about 0.05 and about 5 wt. % of the total diluted composition.

Having generally described the invention, reference is now had to the following examples which are intended to illustrate preferred embodiments but which should not be construed as limiting to the scope of the invention which is defined in the appended claims.

EXAMPLE 1

Preparation of MICROFLEX

Several batches of MICROFLEX were each prepared by mixing 21.3 g of N-methyl pyrrolidone (NMP), 9.3 g of N-octyl pyrrolidone, 9.3 g of EO/PO block copolymer surfactant (PLURONIC L-31*), 56 g of ethoxylated castor oil with 30 EO (Alkamuls EL 620) and 4 g of ethoxylated phosphate ester with 9.7 EO (Rhodafac RS 710). 11.3 g of quizalofop-p-ethyl was dissolved in 88.7 parts of MICROFLEX prepared as above in combination with varying amounts of aromatic oil (Exxon aromatic 200) to produce seven samples, labeled Samples A through G. Another six samples were mixed with aromatic oil (Exxon aromatic 150) and labeled Samples H through M. The stabilities of these samples were compared with an 88.7 parts sample of aromatic oil, Exxon aromatic 150 alone, labeled N and with an 88.7 parts sample of MOSTAR***, a commercially available product, labeled P. Each of the samples A–N and P was mixed at ambient temperature over a period of 3 hours. Stability tests for each of the above samples were conducted for 1 day with the concentrate and for 1 day after dilution with water. The results of these tests are reported in Tables 1 to 4 below.

* supplied by BASF
** supplied by Rhodia
*** Ipesa (Argentina)

TABLE 1

Physical Stability upon Dilution of 11.3 Parts of Quizalofop-P-ethyl Loaded into 88.7 parts of Mixtures of Microflex and Aromatic 200

| Sample | A | B | C | D | E | F | G |
|---|---|---|---|---|---|---|---|
| Microflex 1 | 100 | 90 | 80 | 70 | 60 | 50 | 40 |
| Aromatic 200 | 0 | 10 | 20 | 30 | 40 | 50 | 60 |
| | 100 | 100 | 100 | 100 | 100 | 100 | 100 |

| | Dilution with 1000 ppm Hard Water | | | | | | |
|---|---|---|---|---|---|---|---|
| | A | B | C | D | E | F | G |
| 1:100 dilution | | | | | | | |
| 0 hr | Clear | Clear | Clear | haze | haze | Emulsion | Emulsion |
| 15 minutes | Ppt. | clear | Clear | haze | haze | Emulsion | Emulsion |
| 4 hours | | clear | Clear | haze | haze | 2 phases | 2 phases |
| 1 day | | ppt. | Clear | haze | haze | | |
| 1:400 dilution | | | | | | | |
| 0 hr. | Clear | clear | Clear | opaque | haze | Emulsion | Emulsion |
| 15 minutes | Ppt. | clear | Clear | opaque | haze | Emulsion | Emulsion |
| 4 hours | | clear | Clear | opaque | haze | 2 phases | 2 phases |
| 1 day | | ppt. | Clear | opaque | haze | | |

TABLE 2

Physical Stability upon Dilution of 11.3 Parts of Quizalofop-P-ethyl Loaded into 88.7 parts of Mixtures of Microflex and Aromatic 150

| Sample | H | I | J | K | L | M |
|---|---|---|---|---|---|---|
| Microflex | 100 | 80 | 70 | 60 | 50 | 40 |
| Aromatic 150 | 0 | 20 | 30 | 40 | 50 | 60 |
|  | 100 | 100 | 100 | 100 | 100 | 100 |

Dilution with 1000 ppm Hard Water

1:100 dilution

| | | | | | | |
|---|---|---|---|---|---|---|
| 0 hr. | Clear | Clear | Haze | Emulsion | Emulsion | Emulsion |
| 15 minutes | ppt. | Clear | Haze | emulsion | Emulsion | Emulsion |
| 4 hours | | Clear | Haze | emulsion | 2 phases | 2 phases |
| 1 day | | Clear | Haze | emulsion | | |

1:400 dilution

| | | | | | | |
|---|---|---|---|---|---|---|
| 0 hr. | Clear | Clear | Opaque | emulsion | Emulsion | Emulsion |
| 15 minutes | ppt. | Clear | Opaque | emulsion | Emulsion | Emulsion |
| 4 hours | | Clear | Opaque | emulsion | 2 phases | 2 phases |
| 1 day | | | Opaque | emulsion | | |

TABLE 3

| Sample N | dilution water containing 1000 ppm hard water |
|---|---|
| 1:100 water dilution | |
| 0 hour | Haze |
| 15 minutes | 2 Phases |
| 1:400 water dilution | |
| 0 hour | Haze |
| 15 minutes | 2 Phases |

TABLE 4

| Sample P | dilution water containing 1000 ppm hard water |
|---|---|
| 1:100 water dilution | |
| 0 hour | Haze |
| 15 minutes | Haze |
| 4 hours | 2 Phases |
| 1:400 water dilution | |
| 0 hour | Clear |
| 15 minutes | Clear |
| 4 hours | 2 Phases |

In the above Tables 1 and 2, Samples C–E and I–K remained homogeneous throughout the period tested. After 1 day Sample B precipitated and after 4 hours Samples F, G, L and M separated into 2 phases. Samples N and P, however separated into 2 phases within 3 hours.

The B and C samples of concentrate in table 1 were found to be stable over a period of 2 weeks and these samples remained homogeneous at temperatures of from 15° to 42° C. at both 1:100 to 1:400 water dilution.

EXAMPLE 2

Samples containing 75 part, 70 parts and 60 parts MICROFLEX and the balance in Exxon aromatic 150 (Test 1), and 80 parts, 75 parts, 70 parts and 60 parts MICROFLEX and the balance in Exxon aromatic 200 (Test 2) remained homogeneous at both dilutions over a 4 day period as shown in Table 5.

TABLE 5

Physical Stability upon Dilution of 11.3 Parts of Quizalofop-P-ethyl Loaded into 88.7 parts of Mixtures of Microflex and Aromatic 200 or Aromatic 150

| Microflex | 80 | 75 | 70 | 60 | 75 | 70 | 60 |
|---|---|---|---|---|---|---|---|
| Aromatic 150 | 0 | 0 | 0 | 0 | 25 | 30 | 40 |
| Aromatic 200 | 20 | 25 | 30 | 40 | 0 | 0 | 0 |
| | 100 | 100 | 100 | 100 | 100 | 100 | 100 |

Dilution with 1000 ppm Hard Water

1:100 dilution

| | | | | | | | |
|---|---|---|---|---|---|---|---|
| 0 hr | clear | opaque | Haze | haze | clear | haze | haze |
| 4 days | clear | opaque | Haze | haze | clear | haze | haze |

1:400 dilution

| | | | | | | | |
|---|---|---|---|---|---|---|---|
| 0 hr | clear | clear | Opaque | haze | clear | opaque | haze |
| 4 days | clear | clear | Opaque | haze | clear | opaque | haze |

EXAMPLE 3

Table 6, samples R–Y, comprises the conditions when 4:1 MICROFLEX to oil and when excess oil is used in the concentrate. In all cases, where added emulsifiers were employed, a heterogeneous-solution was obtained upon dilution of the concentrate.

TABLE 6

| | R | S | T | U | V | W | X | Y |
|---|---|---|---|---|---|---|---|---|
| Microflex 1:Aromatic 200 ratio | 8:2 | 7:3 | 6:4 | 5:5 | 4:6 | 3:7 | 2:8 | 1:9 |
| Percent | | | | | | | | |
| Microflex:Aromatic 200 ratio | 33.7 | 33.7 | 33.7 | 33.7 | 33.7 | 33.7 | 33.7 | 33.7 |
| Oleosol 2050 | 35.0 | 35.0 | 35.0 | 35.0 | 35.0 | 35.0 | 35.0 | 35.0 |
| Solvesso 200 | 20.0 | 20.0 | 20.0 | 20.0 | 20.0 | 20.0 | 20.0 | 20.0 |
| Quizalofop-P-ethyl | 11.3 | 11.3 | 11.3 | 11.3 | 11.3 | 11.3 | 11.3 | 11.3 |
| | 100 | 100 | 100 | 100 | 100 | 100 | 100 | 100 |

TABLE 6-continued

| | R | S | T | U | V | W | X | Y |
|---|---|---|---|---|---|---|---|---|
| Dilution with 1000 ppm Hard Water | | | | | | | | |
| 1:100 dilution | | | | | | | | |
| 0 hr | clear | clear | clear | Clear | opaque | opaque | slight haze | emulsion |
| 1 day | clear | clear | clear | Clear | opaque | opaque | slight haze | emulsion |
| 3 days | clear | clear | clear | Clear | haze | haze | haze | emulsion |
| 1:400 dilution | | | | | | | | |
| 0 hr | clear | clear | clear | Clear | clear | clear | opaque | emulsion |
| 3 days | clear | clear | clear | Clear | clear | clear | opaque | emulsion |

What is claimed is:

1. A concentrate of a liquid, water miscible matrix for an agrochemically active compound containing from about 9 to about 25 wt % of the agrochemical wherein the agrochemical is a quinoxalinyl ester selected from the group consisting of quizalofop-p-ethyl ester, quizalofop-p- tefuryl tetrahydrofurfuryl ester, and a $C_1$ to $C_4$ of a halogenated quinoxalinyl oxyphenoxy compound; a mixture of one part of a heavy aromatic petroleum distillate boiling above 100 F and between 1 to 5 parts of a mixture comprising by weight (i) 0 to about 60 of a N-$C_1$ to $C_4$ alkyl lactam (ii) about 0.002 to 40% of a $C_8$ to $C_{18}$ alkyl lactam, (iii) 0 to about 30% of an ethyleneoxide/propyleneoxide block copolymer, (iv) about 0.03 to about 80% of an alkylated castor oil, tristyryl phenol ethoxylate or a mixture thereof and (v) 0 to about 10% of a phosphate ester buffer.

2. The concentrate of claim 1 containing between about by weight 0.15–40% (i), 0.05–29% (ii), 0.5–15% (iii), 40–70% (iv) and 0.005–6% (v).

3. A stable, homogeneous liquid composition comprising the concentrate of one of claims 1 or 2 and between about 0.05 to 25 wt. % of said agrochemically active compound based on total composition.

4. The composition of claim 1 wherein the quinoxalinyl ester is quizalofop-p-ethyl.

5. A stable, homogeneous liquid composition comprising the concentrate of one of claims 1 or 2 which is diluted with up to 99.9 wt. % of water and containing 0.01 to 5 wt. % of said active agrochemical compound based on total diluted concentrate composition.

6. The composition of one of claims 1 or 4 wherein said active agrochemical is a herbicide.

7. A concentrate according to claim 1 wherein the halogenated quinoxalinyl oxyphenoxy compound is selected from the group consisting of chloro quinoxalinyl oxyphenoxy propionate, 2,4-dichloro phenoxy ethyl butyrate, 1,4-dichloro phenoxy ethyl propionate, and 2,4-dichloro phenoxy butyl propionate.

8. A concentrate comprising a liquid, water soluble matrix containing from about 9 to about 25 wt. % of an agrochemically active compound selected from the group consisting of quizalofop-p-ethyl ester, quizalofop-p-tefuryl tetrahydrofurfuryl ester, a $C_1$ to $C_4$ ester of a halogenated quinoxalinyl oxyphenoxy compound and a matrix mixture of 0.2–9 parts of an aromatic petroleum distillate boiling above 100° F. to 1 part of a mixture comprising (i) 0 to about 60% of a N—C to $C_4$ alkyl lactam (ii) about 0.002 to 40% of a $C_8$ to $C_{18}$ alkyl lactam, (iii) 0 to about 30% of an ethyleneoxide/ propyleneoxide block copolymer, (iv) 0.03 to about 80% of an alkylated castor oil, tristyryl phenol ethoxylate or a mixture thereof, and (v) 0 to about 10% and additionally containing 1–60 wt. % of one or more emulsifiers, based on said mixture.

9. A concentrate according to claim 8 wherein the halogenated quinoxalinyl oxyphenoxy compound is selected from the group consisting of chloro quinoxalinyl oxyphenoxy propionate, 2,4-dichloro phenoxy ethyl butyrate, 1,4-dichloro phenoxy ethyl propionate, and 2,4-dichloro phenoxy butyl propionate.

* * * * *